(12) United States Patent
Veerappan et al.

(10) Patent No.: US 9,580,414 B2
(45) Date of Patent: Feb. 28, 2017

(54) SALTS AND HYDRATES OF ANTIPSYCHOTICS

(71) Applicant: SHASUN PHARMACEUTICALS LIMITED, Chennai (IN)

(72) Inventors: Vijayabaskar Veerappan, Chennai (IN); Srimurugan Sankareswaran, Chennai (IN); Sathish Kumar Raman Viswanathan, Chennai (IN); N. Subramanian, Chennai (IN)

(73) Assignee: Shasun Pharmaceuticals Limited, Chennai (IN)

( * ) Notice: Subject to any disclaimer, the term of this patent is extended or adjusted under 35 U.S.C. 154(b) by 0 days.

(21) Appl. No.: 14/415,995

(22) PCT Filed: Jul. 18, 2013

(86) PCT No.: PCT/IB2013/055908
§ 371 (c)(1),
(2) Date: Jan. 20, 2015

(87) PCT Pub. No.: WO2014/013465
PCT Pub. Date: Jan. 23, 2014

(65) Prior Publication Data
US 2015/0175596 A1 Jun. 25, 2015

(30) Foreign Application Priority Data

Jul. 18, 2012 (IN) .............................. 2896/CHE/2012

(51) Int. Cl.
*C07D 417/12* (2006.01)
*C07D 417/14* (2006.01)

(52) U.S. Cl.
CPC ......... *C07D 417/14* (2013.01); *C07D 417/12* (2013.01); *C07B 2200/13* (2013.01)

(58) Field of Classification Search
CPC ........................... C07D 417/12; C07D 417/14
See application file for complete search history.

(56) References Cited

U.S. PATENT DOCUMENTS

| | | | |
|---|---|---|---|
| 8,981,095 B2 * | 3/2015 | Marom | ........... C07D 209/44 544/368 |
| 2005/0020608 A1 | 1/2005 | Reddy et al. | |
| 2006/0211699 A1 | 9/2006 | Iera et al. | |

FOREIGN PATENT DOCUMENTS

| | | |
|---|---|---|
| CN | 102827157 A | 12/2012 |
| WO | WO-2012/063246 A1 | 5/2012 |

OTHER PUBLICATIONS

Yan et al., 2012, caplus an 2012:1874546.*
International Search Report for PCT/IB2013/055908, mailed on Jan. 15, 2014.

* cited by examiner

*Primary Examiner* — Sun Jae Yoo
(74) *Attorney, Agent, or Firm* — McCarter & English, LLP; Cristin H. Cowles; Jill A. Mello

(57) ABSTRACT

The present invention relates to a novel salt of (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione and hydrates thereof, to methods for preparing the novel salt and its hydrates. In one aspect, the present invention provides a compound which is lurasidone dihydrochloride. In another aspect, the present invention provides a process for preparation of lurasidone dihydrochloride comprising: (i) mixing lurasidone free base in an organic solvent system; (ii) subjecting step (i) mixture to acid proton source; and (iii) isolating compound of lurasidone dihydrochloride.

5 Claims, 4 Drawing Sheets

SALTS AND HYDRATES OF ANTIPSYCHOTICS

CROSS-REFERENCE TO RELATED APPLICATIONS

This application is a 35 U.S.C. §371 national stage filing of International Application No. PCT/IB2013/055908, filed on Jul. 18, 2013, which claims priority to Indian Patent Application No. 2896/CHE/2012, filed on Jul. 18, 2012. The entire contents of each of the foregoing applications are incorporated herein by reference.

TECHNICAL FIELD

The present invention relates to a novel salt of (3aR,4S, 7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione and hydrates thereof, to methods for preparing the novel salt and its hydrates.

BACKGROUND OF THE INVENTION

Lurasidone is an atypical antipsychotic developed by Dainippon Sumitomo Pharma for the treatment of Schizophrenia and bipolar disorders.

Lurasidone HCl is chemically known as (3aR,4S,7R, 7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione hydrochloride.

Lurasidone hydrochloride and the processes for its preparation are disclosed in U.S. Pat. No. 5,532,372. While several organic and inorganic acids are mentioned as possible salt-forming agents, including hydrochloric acid, there is no mention of particular dihydrochloride salt which is the subject of the present application.

The marketed product, Latuda, is the monohydrochloride salt described above. Lurasidone hydrochloride is very slightly soluble in water, practically insoluble in 0.1 N HCl hence having poor bioavailability of less than 12%. For development of pharmaceutical formulations, particularly oral dosage forms, the active ingredient must have sufficient oral bioavailability. There is a demand in the art for a new Lurasidone salt, which would be more soluble, stable with remarkable pharmacokinetic properties and more suitable for technological processing, than hydrochloride salt which is used in the marketed pharmaceutical formulations.

These alternative salts and salt forms must also pass the quality and safety criteria set out by the various health authorities worldwide and can themselves be marketed as equally efficacious and often more cost effective alternatives to patient groups and healthcare services.

The formation of salts of Lurasidone with the desired advantageous properties has proved to be difficult. The inventors have succeeded in preparing novel Lurasidone salt and different forms of said novel salt. Extensive research has shown that the salts of Lurasidone according to the invention have proved to be that possess high water solubility particularly compared with the hydrochloride salt forms of Lurasidone and its free base. The water solubility of the new Lurasidone salts and hydrates makes the new compounds particularly suitable for human consumption.

SUMMARY OF THE INVENTION

Accordingly, there is provided a compound of formula (I)

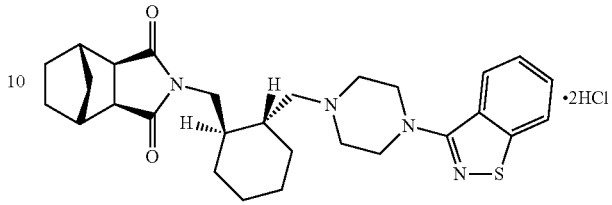

Formula-I in a first aspect of the invention.

A second aspect of the invention provides that the compound of formula (I) is crystalline.

A third aspect of the invention provides that the compound of formula (I) is hydrate. Preferably, the hydrate is dihydrate.

One embodiment of the second aspect of the invention provides that the compound of formula I, having an X-ray diffraction pattern substantially as shown in FIG. 1.

In another embodiment of the second aspect of the invention provides that the compound of formula I, having a differential scanning calorimetry thermogram substantially as shown in FIG. 2.

Yet another embodiment of the second aspect of the invention provides that the compound of formula I, having a thermo gravimetric analysis thermogram substantially as shown in FIG. 3.

A fourth aspect according to the invention provides process for preparing the compound of formula I comprising:
(i) Mixing free base of compound I in an organic solvent system;
(ii) Subjecting step (i) mixture to acid proton source;
(iii) Isolating the compound I.

A fourth aspect according to the invention provides process for preparing Lurasidone dihydrochloride comprising:
(i) Mixing mono hydrochloride salt of compound I in an organic solvent system;
(ii) Subjecting the step (i) mixture to acid proton source;
(iii) Isolating the compound I.

BRIEF DESCRIPTION OF THE ACCOMPANYING DRAWINGS

DESCRIPTION OF THE INVENTION

The term "compound I" as used herein throughout the description and claims is intended to mean Lurasidone dihydrochloride and/or any hydrates, or polymorphs unless otherwise specified or stated.

The term "purity" as used herein throughout the description and claims refers to chemical purity and/or polymorphic purity. Chemical purity may be determined for example by HPLC and polymorphic purity may be determined by XRPD analysis.

Accordingly, there is provided a compound of formula (I)

Formula-I

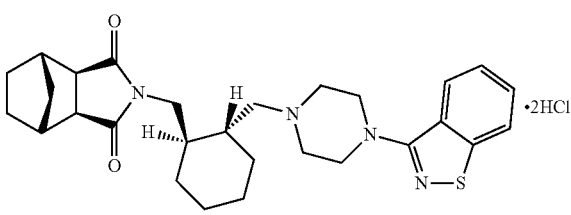

in a first aspect of the invention.

A second aspect of the invention provides that the compound of formula (I) is crystalline.

A third aspect of the invention provides that the compound of formula (I) is hydrate. Preferably, the hydrate is dihydrate.

Figure 1:
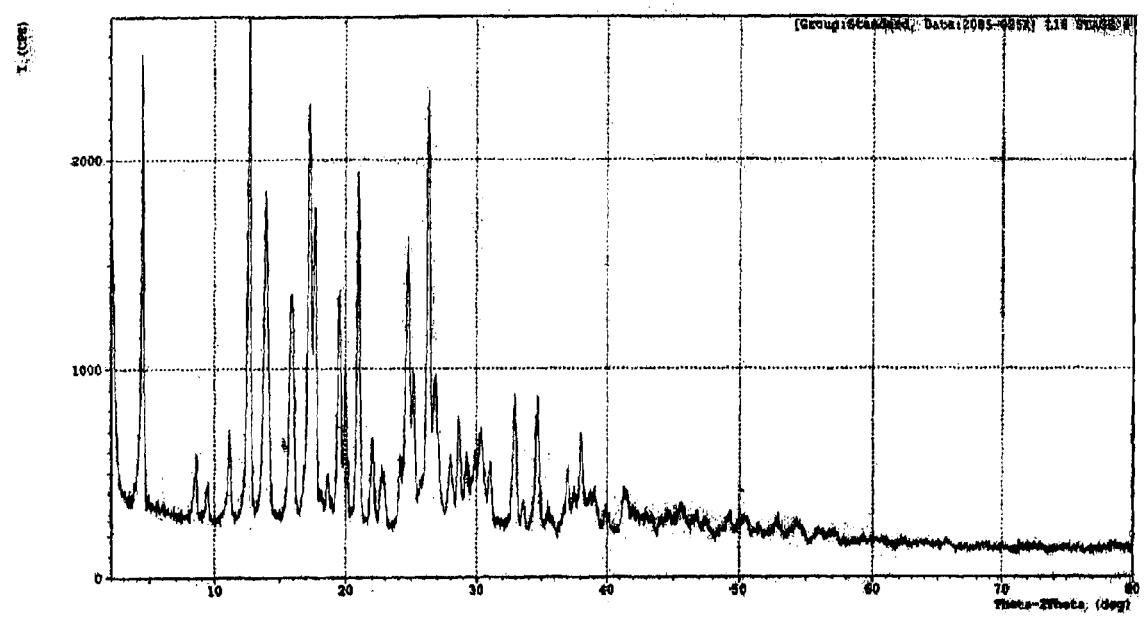
FIG. 1 is a representative X-ray diffraction pattern of compound I according to the invention.

One embodiment of the second aspect of the invention provides crystalline compound I, preferably having an X-ray diffraction pattern comprising peaks at 4.4, 12.6, 13.9, 26.2, 20.9, 17.2±0.2 degrees 2-theta. A particularly preferred embodiment provides compound I having an X-ray diffraction pattern comprising further peaks at 4.4, 12.6, 13.9, 15.8, 17.2, 17.6, 19.4, 19.9, 20.9, 24.6, 25.1, 25.7, 26.2±0.2 degrees 2-theta. Preferably the compound I of the second aspect of the invention has an X-ray diffraction pattern substantially as shown in FIG. 1.

Figure 2:
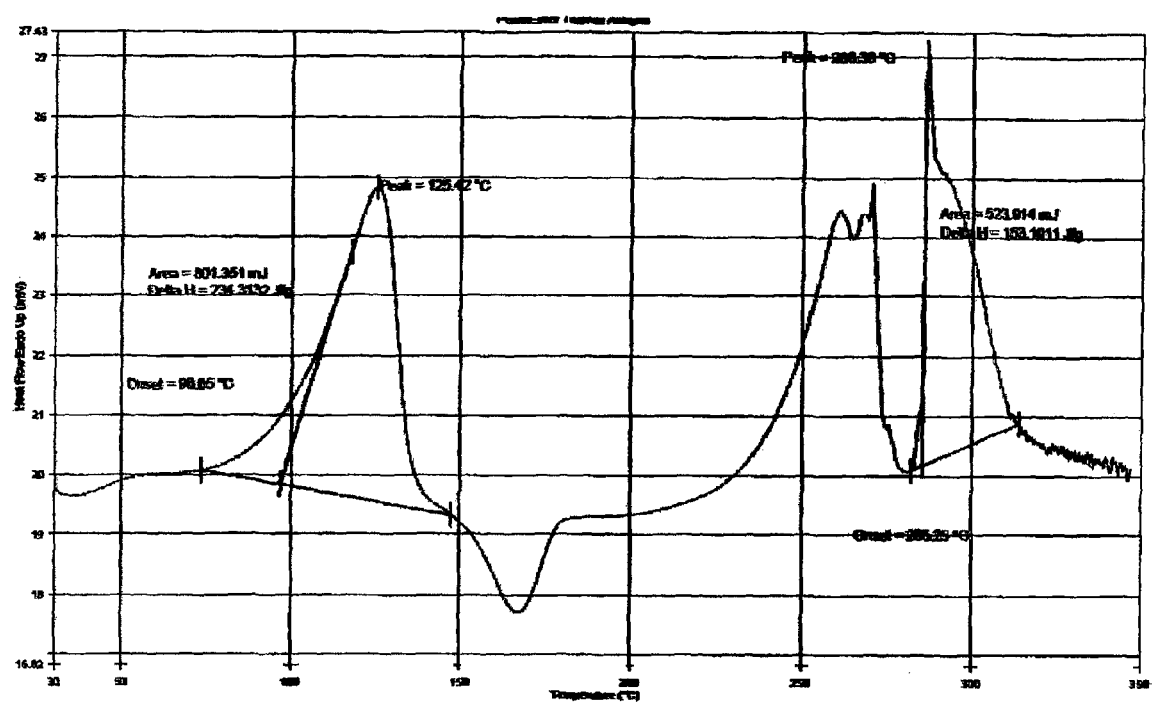
FIG. 2 is a representative differential scanning calorimetry thermogram of compound I according to the invention.

In another embodiment of the second aspect of the invention is provided having a differential scanning calorimetry thermogram with endothermic peaks at about 125° C.±2° C. and 286° C.±2° C. Preferably the crystalline compound I of the second aspect of the invention has a differential scanning calorimetry thermogram substantially as shown in FIG. 2.

Figure 3:
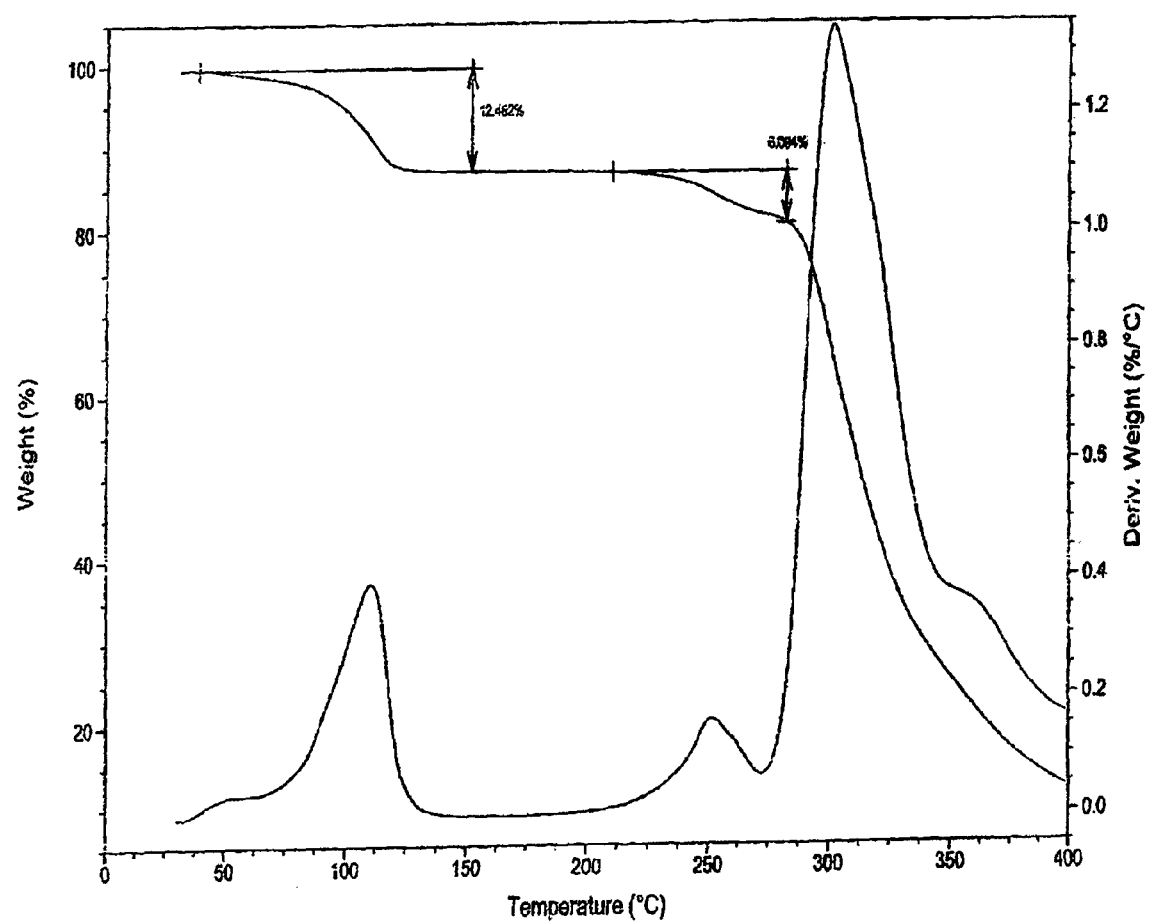
FIG. 3 is a representative thermogravimetry curve of compound I according to the invention.
Figure 4:
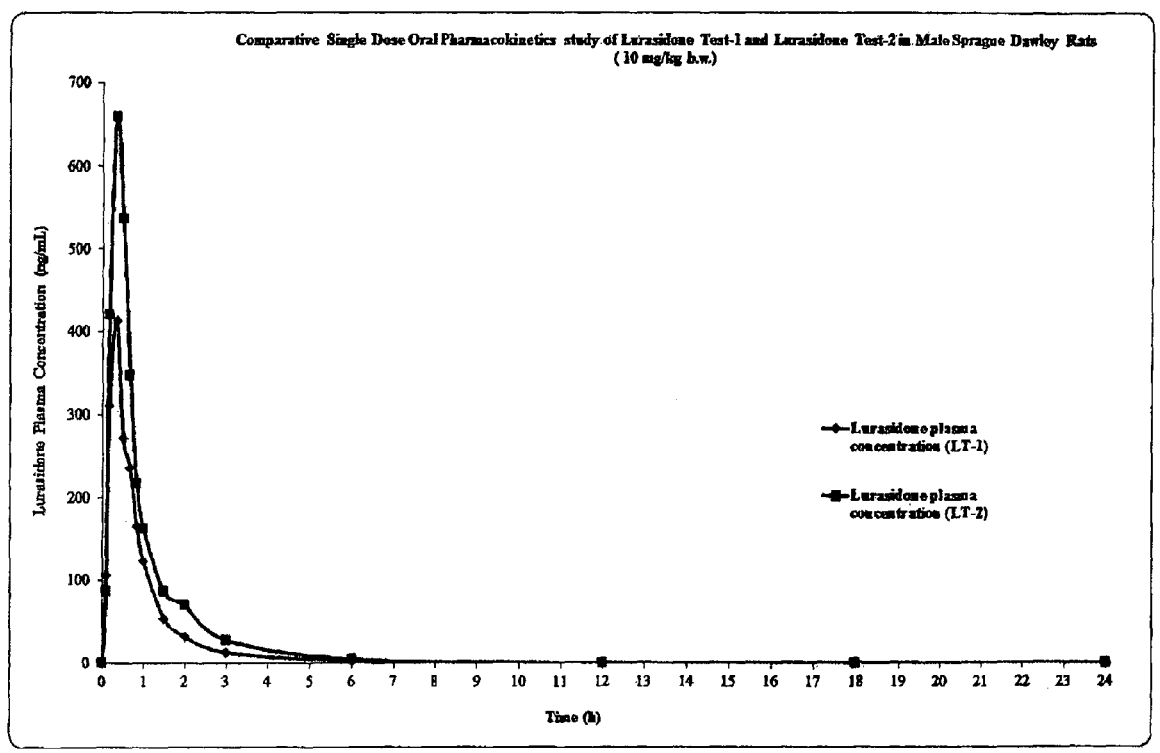
FIG. 4 represents oral PK study of Lurasidone monohydrochloride v. dihydrochloride comparative plasma concentration (ng/mL) Vs time (h) profile.

A further embodiment of the second aspect of the invention provides compound I having a thermo gravimetric analysis thermogram substantially as shown in FIG. 3.

In accordance with the present invention, there is provided compound I exhibits additional characteristic analytical data i.e., IR data in a potassium bromide compressed tablet shows the following significant bands expressed in reciprocal wave numbers (cm-1): IR (KBr): 3355, 2944, 2876, 2596, 1766, 1695, 1571, 1551, 1437, 1372, 1300, 1264, 1186, 1142, 952, 775, 732 cm-1 compared to monohydrochloride form of Lurasidone i.e., 1762, 1687, 1502, 1556, 1430, 1390, 1367, 1287, 1183, 1135, 975, 778, 742.

Preferably, the first aspect of the invention provides compound I having a purity of greater than 95%, preferably greater than 99%, most preferably greater than 99.5% and it is suitable for use in medicine.

A third aspect according to the invention provides process for preparing compound I comprising:
(i) Mixing free base of compound I in an organic solvent system;
(ii) Subjecting step (i) mixture to acid proton source
(iii) Isolating compound I.

A fourth aspect according to the invention provides process for preparing compound I comprising:
(i) Mixing hydrochloride salt of compound I in an organic solvent system;

(ii) Subjecting step (i) mixture to acid proton source
(iii) Isolating the compound I.

The chemical synthesis of starting free base or hydrochloride salt of compound I may be affected by any method known in the art. For example, the synthesis described in U.S. Pat. No. 5,532,372 cited above and incorporated by reference herein in its entirety, may be used for this purpose. Also, the high pure free base of compound I and its hydrochloride salt may be used for this purpose according to the invention claimed in our co-pending Indian application 2411/CHE/2012.

For the purposes of the invention, particularly the third and fourth aspect, the term "mixing" is meant to include any addition of free base of compound I to an organic solvent system; this may include dissolving or suspending all or any proportion of the free base of compound I in the solvent system. In certain embodiments the addition of the free base of compound I to the solvent system may result in a suspension or the free base may be dissolved completely or partially in the solvent system.

In a preferred embodiment of this invention, the acid proton source comprises of hydrochloric acid. Preferably, the acid proton source introduced to the reaction mixture may be concentrated hydrochloric acid or dry gas. The aforesaid concentrated hydrochloric acid may be dissolved in organic solvent or passed as dry gas to the reaction mixture of step (i). Preferably, the acid proton source required according to the invention would be the amount sufficient to form compound I.

In certain embodiments of the third and fourth aspect, the organic solvent system comprises a ketone (such as acetone), a nitrile (such as acetonitrile), ether (such as diethyl ether), an ester (such as ethyl acetate), chlorinated solvents or mixtures thereof. Preferably the organic solvent system comprises acetone, acetonitrile, tetrahydrofuran, ethyl acetate or mixtures thereof.

The dihydrochloride salt of the present invention show excellent solubility in water as well as in mixtures of water with other pharmaceutically acceptable solvents miscible with water. In particular, the solubility of the compounds of the present invention in comparison with hydrochloride was assayed in water and recorded.

The results obtained show that Lurasidone hydrochloride solubility in either solutions is less than 0.212 mg/ml with a pH of about 3.8, the solubility of the compounds of the present invention of the obtained solutions are appreciable.

The solubility study was performed for the dihydrochloride salt of the present invention using the McIlvaine Buffer pH 3.8. In particular, the salts obtained through the process, disclosed in the examples 3, 7 & 13 shows excellent solubility about 0.647 to about 0.902 (mg/ml) when compared against the mono hydrochloride salt showing solubility around 0.212 (mg/ml).

TABLE 1

Comparative Solubility Profile of Lurasidone monohydrochloride and dihydrochloride

| Batch. No | Active Pharmaceutical Ingredient | Solubility (mg/ml) | | |
|---|---|---|---|---|
| | | Sample 1 | Sample 2 | Avg. |
| 2125 085 | Mono HCl Salt | 0.2104 | 0.2148 | 0.2126 |
| 2085 055 | Di HCl Salt | 0.7220 | 0.5724 | 0.6472 |
| 2548 061 | Di HCl Salt | 0.9548 | 0.8498 | 0.9020 |

The dihydrochloride salt of the present invention are tested for stability by storage in an adverse environment, such as the widely used 40° C., 75% relative humidity ("RH") accelerated stability testing conditions 50° C., 90% relative humidity ("RH") and it has excellent stability profile and it is susceptible for several factors including the moisture, heat, and light may initiate and/or accelerate the chemical interaction thereby degrading the purity of the final compound.

Lurasidone salts mean plasma PK parameters were quantified with an API 3200 LC-MS/MS system and illustrated in Table 1.

After administration of the test item, the animals were observed for clinical signs of toxicity and mortality/morbidity. No mortality was observed after administration of the test item till the completion of the study. No adverse clinical signs were observed after administration of both the test items except for mild grooming observed in 4 animals after administration of the test item and it can be considered as incidental finding.

Study results further revealed that dihydrochloride salt showing excellent Pharmacokinetic properties of higher Cmax, AUC of 659.34 (ng/ml) than monohydrochloride salt. Further Dihydrochloride salt showing better bioavailability of higher AUC values of AUClast (h*ng/mL) 569.83 and AUCinf (h*ng/mL) 577.30.

TABLE 2

Oral PK Study of Lurasidone salts & its comparative plasma PK parameters
Mean plasma PK parameters of Lurasidone salts

| Parameters | Monohydrochloride | Dihydrochloride |
|---|---|---|
| Dose (mg/kg b.w.) | 10.00 | 10.00 |
| $C_{max}$ (ng/mL) | 412.39 | 659.34 |
| $T_{max}$ (h) | 0.33 | 0.33 |
| $AUC_{last}$ (h * ng/mL) | 352.41 | 569.83 |
| $AUC_{inf}$ (h * ng/mL) | 357.32 | 577.30 |
| $AUC_{extrap}$ (%) | 1.37 | 1.29 |
| $T_{1/2}$ (h) | 1.19 | 1.07 |
| $MRT_{last}$ (h) | 0.95 | 1.05 |

The following non-limiting examples illustrate specific embodiments of the present invention. They are not intended to limit the scope of the present invention in any way.

EXAMPLES

Example-1

Preparation of Lurasidone Dihydrochloride Dihydrate in DCM Using Con.HCl

To a solution of (3aR,4S,7R,7aS)-2-{(1R,2R)-2-[4-(1,2-benzisothiazol-3-yl)piperazin-1-ylmethyl] cyclohexylmethyl}hexahydro-4,7-methano-2H-isoindole-1,3-dione (Lurasidone freebase, 5.0 g (0.0101 moles)) in 50.0 ml of DCM was added with Con.HCl (35.0%), 4.21 g (0.0404 moles) slowly over a period of 10 min at 30-32° C. Stirred the reaction mass for about 2 h at 30-32° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (5.2 g, 1.04 w/w; 85%). The dried solid prepared according to the present invention subjected to XRPD, DSC, TGA, KF, HCl content and chloride content analyses, which all confirmed that the precipitated solid was Lurasidone dihydrochloride dihydrate.

Example-2

Preparation of Lurasidone Dihydrochloride Dihydrate in DCM Using Ethyl Acetate HCl To a solution of (3aR,4S,7R,7aS)-2-{(1R,2R)-2-[4-(1,2-benzisothiazol-3-yl)piperazin-1-ylmethyl] cyclohexylmethyl}hexahydro-4,7-methano-2H-isoindole-1,3-dione (Lurasidone freebase), 5.0 g (0.0101 moles) in 50.0 ml of DCM was added ethyl acetate HCl (~20.0%), 3.86 g (0.0212 moles) slowly over a period of 10 min at 30-32° C. Stirred the reaction mass for about 6 h at 30-32° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-2H-isoindole-1,3-dione dihydrochloride dihydrate (Lurasidone dihydrochloride dihydrate) as a white solid (5.0 g, 1.0 w/w; 81.9%).

Example-3

Preparation of Lurasidone Dihydrochloride Dihydrate in DCM Using Ether HCl

To a solution of (3aR,4S,7R,7aS)-2-{(1R,2R)-2-[4-(1,2-benzisothiazol-3-yl)piperazin-1-ylmethyl] cyclohexylmethyl}hexahydro-4,7-methano-2H-isoindole-1,3-dione (Lurasidone freebase), 5.0 g (0.0101 moles) in 50.0 ml of DCM was added ether HCl (~25.0%), 3.08 g (0.0212 moles) slowly over a period of 10 min at 30-32° C. Stirred the reaction mass for about 6 h at 30-32° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl] cyclohexylmethyl}hexahydro-4,7-methano-2H-isoindole-1,3-dione dihydrochloride dihydrate (Lurasidone dihydrochloride dihydrate) as a white solid (4.9 g, 0.98 w/w; 80.0%).

Example-4

Preparation of Lurasidone Dihydrochloride Dihydrate in DCM Using Dry HCl Gas

To a solution of (3aR,4S,7R,7aS)-2-{(1R,2R)-2-[4-(1,2-benzisothiazol-3-yl)piperazin-1-ylmethyl] cyclohexylmethyl}hexahydro-4,7-methano-2H-isoindole-1,3-dione (Lurasidone freebase), 5.0 g (0.0101 moles) in 50.0 ml of DCM, dry HCl gas purged for about 15 min at 20-25° C. Slowly raised mass temperature to 30-32° C. over a period of 20 min. Stirred the reaction mass for about 3 h at 30-32° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl) piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (3.0 g, 0.60 w/w; 49.1%)

Example-5

Preparation of Lurasidone Dihydrochloride Dihydrate in DCM Using Con.HCl

To a solution of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione (Lurasidone freebase), 5.0 g (0.0101 moles) in 50.0 ml of DCM was cooled to 0-5° C. and added Conc.HCl (35.0%), 2.19 g (0.0212 moles) slowly over a period of 10 min at 0-5° C. Stirred the reaction mass for about 2 h at 0-5° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (4.0 g, 0.80 w/w; 65.5%)

Example-6

Preparation of Lurasidone Dihydrochloride Dihydrate in DCM Using Con.HCl

To a solution of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione (Lurasidone freebase), 5.0 g (0.0101 moles) in 50.0 ml of DCM was heated to vigorous reflux (40-42° C.) was added Conc.HCl (35.0%) at reflux, 4.21 g (0.0404 moles) slowly over a period of 10 min at reflux. Stirred the reaction mass for about 2 h at vigorous reflux. Cooled to 30-32° C., filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (5.1 g, 1.02 w/w; 83.6%).

Example-7

Preparation of Lurasidone Dihydrochloride Dihydrate in Ethyl Acetate Using Ethyl Acetate HCl

To slurry of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione (Lurasidone freebase), 5.0 g (0.0101 moles) in 25.0 ml of ethyl acetate was heated to 35-37° C. and added ethyl acetate HCl (~20.0%), 3.85 g (0.0212 moles) slowly over a period of 10 min at 35-37° C. Cooled to 30-32° C. Stirred the reaction mass for about 5 h at 30-32° C. Filtered the solid and washed with 10 ml of ethyl acetate. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (5.0 g, 1.0 w/w; 81.9%).

Example-8

Preparation of Lurasidone Dihydrochloride Dihydrate in Ethyl Acetate and DCM Mixture Using Con.HCl

To a mixture of ethylacetate 35.0 ml and Conc.HCl (35.0%), 4.21 g (0.0404 moles), added a solution of 3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione (Lurasidone freebase), 5.0 g (0.0101 moles) in 15.0 ml of DCM slowly over a period of 20 min at 45-50° C. The reaction mass was stirred for about 1 h at 45-50° C., cooled to 30-32° C. and further stirred for about 1 h at same temperature. Filtered the solid and washed with 10.0 ml of ethyl acetate. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (5.4 g, 1.08 w/w; 88.5%).

Example-9

Preparation of Lurasidone Dihydrochloride Dihydrate in Acetone by Using Ethyl Acetate HCl

To a solution of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione (Lurasidone freebase), 5.0 g (0.0101 moles) in 25.0 ml of acetone was added ethylacetate HCl (~20.0%), 3.85 g (0.0212 moles) slowly over a period of 10 min at 30-32° C. Stirred the reaction mass for about 2 h at 30-32° C. Filtered the solid and washed with 10 ml of prechilled acetone. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (2.0 g, 0.4 w/w; 32.7%)

Example-10

Preparation of Lurasidone Dihydrochloride Dihydrate in Acetonitrile by Using Ethyl Acetate HCl

To a solution of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione (Lurasidone freebase), 5.0 g (0.0101 moles) in 25.0 ml of acetonitrile was added ethylacetate HCl (~20.0%), 3.85 g (0.0212 moles) slowly over a period of 10 min at 30-32° C. Stirred the reaction mass for about 2 h at 30-32° C. Filtered the solid and washed with 10 ml of prechilled acetonitrile. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (2.1 g, 0.42 w/w; 34.4%)

Example-11

Preparation of Lurasidone Dihydrochloride Dihydrate in DCM by Using Con.HCl from Lurasidone Hydrochloride

To a solution of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione hydrochloride (Lurasidone hydrochloride), 5.0 g (0.0093 moles) in 50.0 ml of DCM was added Con.HCl (~35.0%), 1.92 g (0.0186 moles) slowly over a period of 10 min at 30-32° C. Stirred the reaction mass for about 2 h at 30-32° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (3.0 g, 0.60 w/w; 52.6%)

Example-12

Preparation of Lurasidone Dihydrochloride Dihydrate in Ethyl Acetate by Using Con.HCl from Lurasidone Hydrochloride To slurry of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione hydrochloride (Lurasidone hydrochloride), 5.0 g (0.0093 moles) in 50.0 ml of ethyl acetate was added Con.HCl (~35.0%), 1.92 g (0.0186 moles) slowly over a period of 10 min at 30-32° C. Stirred the reaction mass for about 2 h at 30-32° C. Filtered the solid and washed with 10 ml of ethyl acetate. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (3.2 g, 0.64 w/w; 56.3%)

Example-13

Preparation of Lurasidone Dihydrochloride Dihydrate in DCM by Using Ethyl Acetate HCl from Lurasidone Hydrochloride To a solution of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione hydrochloride (Lurasidone hydrochloride), 5.0 g (0.0093 moles) in 50.0 ml of DCM was added ethyl acetate HCl (~20.0%), 3.38 g (0.0186 moles) slowly over a period of 10 min at 30-32° C. Stirred the reaction mass for about 2 h at 30-32° C. Filtered the solid and washed with 10 ml of DCM. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (2.9 g, 0.58 w/w; 51.0%)

Example-14

Preparation of Lurasidone Dihydrochloride Dihydrate in Ethyl Acetate by Using Ethyl Acetate HCl from Lurasidone Hydrochloride To slurry of (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione hydrochloride (Lurasidone hydrochloride), 5.0 g (0.0093 moles) in 50.0 ml of ethyl acetate added ethyl acetate HCl (~20.0%), 3.38 g (0.0186 moles) slowly over a period of 10 min at 30-32° C. Stirred the reaction mass for about 2 h at 30-32° C. Filtered the solid and washed with 10 ml of ethyl acetate. The solid was dried under vacuum at 40-45° C. for 6 h to get (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione dihydrochloride dihydrate (Lurasidone dihydrochloride dihydrate) as a white solid (3.3 g, 0.66 w/w; 58.0%).

Example-15

Single Dose Oral Pharmacokinetics Comparative Study of Lurasidone Monohydrochloride v. Dihydrochloride in Male Sprague Dawley Rats Male Sprague Dawley rats aged 6-8 weeks and weighing 180-220 g will be used for experiment. Animals will be acclimatized for a minimum period of 5 days. Overnight fasted animals were administered the test substance by oral gavage with a dose equivalent dose of 10 mg/kg of the parent compound with ready to use formulation provided and at a dose volume of 10.06 & 9.6 mL/kg b.w. With mild inhalation anesthesia (Isoflurane), blood samples (200-250 µL) were collected by retro-orbital route at specified time points. Lurasidone hydrochloride and dihydrochloride samples were administered by oral route at a dose volume of 10.06 & 9.6 mL/kg body weight respectively. The actual dosage volume for each animal were calculated based on the fasted body weight. All the animals were administered a single dose on the day of experiment. Blood samples were collected in pre-labeled centrifuge tubes containing anticoagulant (K2EDTA). Blood sampling time points for both the groups were as follows Group 1 & 2—Subgroup 1 (n=5)—0.08, 0.16, 0.33, 0.5, 0.67, 0.83, 1.00 & Subgroup 2 (n=5)—1.5, 2, 3, 6, 12, 18, 24 h. All the animals were administered a single dose on the day of experiment. Blood samples were centrifuged at 4000 rpm at 4° C. for 10 minutes and the corresponding plasma samples were harvested into pre-labeled tubes. Plasma samples will be stored at −80° C. until analysis. The blood samples were centrifuged at 4000 rpm for 10 minutes at 4° C. and the corresponding plasma samples were transferred to clean pre-labeled tubes and stored at −80° C. until analysis.

We claim:
1. A compound of Formula-I

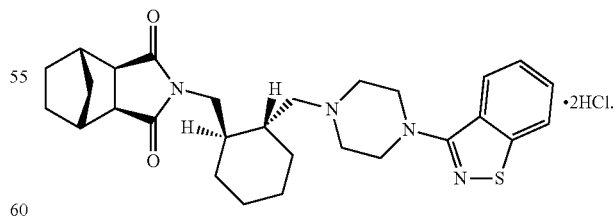

2. The compound according to claim 1, wherein said compound is crystalline.
3. The compound according to claim 1, wherein said compound is a hydrate.
4. The compound of claim 3, wherein said hydrate is dihydrate.

5. The compound according to claim 4 having an X-ray diffraction pattern comprising peaks at 4.4±0.2, 12.6±0.2, 13.9±0.2, 26.2±0.2, 20.9±0.2 and 17.2±0.2 degrees 2θ.

* * * * *